United States Patent [19]

Hori et al.

[11] Patent Number: 4,981,680
[45] Date of Patent: Jan. 1, 1991

[54] P-HYDROXYCINNAMAMIDE DERIVATIVES AND MELANIN INHIBITOR COMPRISING THE SAME

[75] Inventors: Kimihiko Hori, Utsunomiya; Koichi Nakamura, Wakayama; Michio Kawai, Funabashi; Itsuro Motegi, Utsunomiya; Genji Imokawa, Utsunomiya; Naotake Takaishi, Utsunomiya, all of Japan

[73] Assignee: Kao Corporation, Tokyo, Japan

[21] Appl. No.: 380,518

[22] Filed: Jul. 17, 1989

Related U.S. Application Data

[62] Division of Ser. No. 76,872, Jul. 23, 1987, Pat. No. 4,876,084.

[30] Foreign Application Priority Data

Aug. 4, 1986 [JP] Japan ............................... 61-183068
Apr. 9, 1987 [JP] Japan ................................. 62-87815

[51] Int. Cl.$^5$ .............................................. A61K 7/48
[52] U.S. Cl. ..................................... 424/62; 514/622
[58] Field of Search ................... 424/62; 514/617, 622

[56] References Cited

FOREIGN PATENT DOCUMENTS 2141626  1/1985  United Kingdom ................. 424/62

OTHER PUBLICATIONS

CA90(23):187307d Van Brussel, W and Vznsumere, C. F. 1979.

Primary Examiner—Merrell C. Cashion, Jr.
Assistant Examiner—Susan S. Rucker
Attorney, Agent, or Firm—Oblon, Spivak, McClelland, Maier & Neustadt

[57] ABSTRACT

A novel melanin inhibitor comprising as an active component a p-hydroxycinnamamide derivative of the following general formula (I)

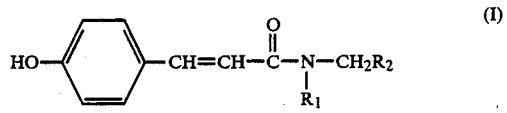

in which $R_1$ represents a hydrogen atom or a 2-hydroxyethyl group, and $R_2$ represents a hydroxymethyl group or a carboxyl group.

The melanin inhibitor may take various forms such as a lotion, an emulsion, a cream, an ointment, a gel and the like, and it is locally applied onto affected parts such as spots and freckles on the skin, and a pigmental deposition after sunburn.

1 Claim, No Drawings

P-HYDROXYCINNAMAMIDE DERIVATIVES AND MELANIN INHIBITOR COMPRISING THE SAME

This is a division, of application Ser. No. 07/076,872, filed on July 23, 1987, now U.S. Pat No. 4,876,084.

BACKGROUND OF THE INVENTION

1. Field of the Invention

This invention relates to novel p-hydroxycinnamamide derivatives and also to a melanin inhibitor comprising the same as an active component.

2. Description of the Prior Art

The color of the skin is chiefly influenced by the amount of melanin in the epidermis. This melanin is invariably produced within the melanocytes and is released toward surrounding corneocytes, and thus falls off as the cornification proceeds, so that the density within the epidermis is maintained constant. Accordingly, the skin color becomes uniform and little change in the color is recognized through a year. However, the melanin production mechanism is promoted by the action of UV rays and a melanocyte stimulating hormone (MSH) or by ageing, and the skin is clinically melanized. If the melanization takes place locally, a clear difference from a surrounding normal skin appears and may result in pigmental spots such as freckles or chloasma.

These spots, freckles, chloasma, and pigmentation after sunburn tend to occur and increase with aging or become more difficult to disappear, and have been one of typical skin troubles of aged persons.

Accordingly, there is a strong demand for a medicine which is able to return the pigmental spots to the surrounding normal skin color.

For this purpose, a variety of medicines have been proposed and some have been in use. For instance, peroxides are considered to have the action of bleaching the produced melanin. Attempts have been made to use hydrogen peroxide, benzoyl peroxide, and the like. However, these compounds are very unstable and have not been recognized to show the practical effect of preventing the pigmental deposition. In recent years, cosmetics containing vitamin C (L-ascorbic acid) having good reducing ability have been used, but the vitamin C is not so stable and does rarely show an appreciable effect. In Europe and the United States of America, hydroquinone and derivatives thereof, and various catechols have been used to cure spots or as medicines for bleaching of colored person's skin. These compounds however, leave much to be desired from the standpoint of safety because they may sometimes cause irritation and allergy. Besides, in some cases, they produce vitiligo thus being difficult for use as a melanin inhibitor. Aside from the above, a variety of melanin inhibitors (or bleaching cosmetics) have been reported but few are safe and show a substantial effect of improving the pigmental deposition.

The present inventors proposed in our Japanese patent application Laid-open No. 60-190713 p-hydroxycinnamamide derivatives of the following formula (a)

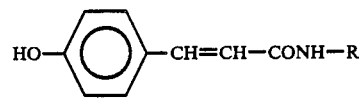

in which R represents a hydrogen atom, and an alkyl, cycloalkyl or alkenyl group having from 1 to 24 carbon atoms, these derivatives having the melanin inhibiting action.

However, these compounds were not satisfactory with respect to the miscibility with other ingredients when formulated in cosmetics and the percutaneous absorptivity.

SUMMARY OF THE INVENTION

Under these circumstances in the art, the present inventors made further studies and found that p-hydroxycinnamamide derivatives of the general formula (I) shown below have a better melanin inhibiting action than the compounds of the formula (a) and have better miscibility with other ingredients used in cosmetics. These derivatives do not develop skin stimulation and allergy at all. The present invention was accomplished based on the above finding.

According to the invention, there is provided a melanin inhibitor which comprises, as an active component, a p-hydroxycinnamamide derivative of the following general formula (I)

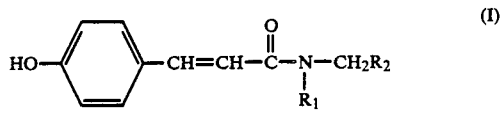

in which $R_1$ represents a hydrogen atom or a 2-hydroxyethyl group, and $R_2$ represents a hydroxymethyl group or a carboxyl group.

DETAILED DESCRIPTION OF THE INVENTION AND PREFERRED EMBODIMENTS

Of the p-hydroxycinnamamide derivatives of the general formula (I), a compound of the following formula (II) is a novel compound

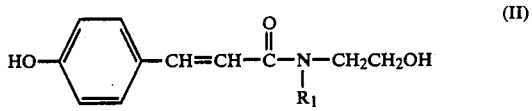

in which $R_1$ is a hydrogen atom or a 2-hydroxyethyl group. Accordingly, the present invention also provides a novel p-hydroxycinnamamide derivative of the formula (II).

N-(p-hydroxycinnamoyl)glycine of the following formula (III) is within the scope of the effective melanin inhibitors used in the present invention and is a known compound

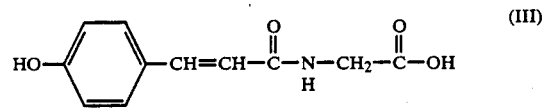

This compound can be readily prepared, for example, according to the following reaction sequence

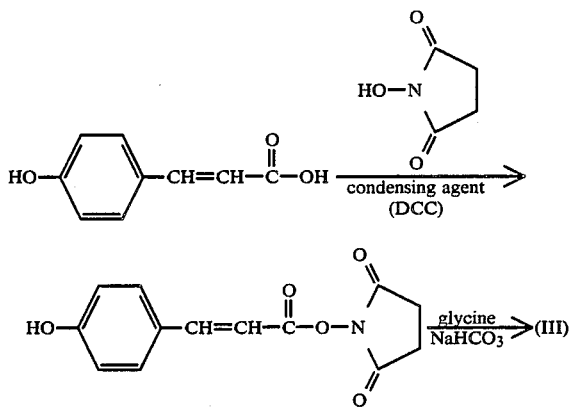

The preparation of the novel p-hydroxycinnamamide derivative (II) according to the invention is not critical. For instance, the derivative (II) is prepared according to the following reaction scheme in which mono or diethanolamine (V) is reacted with a p-acetoxycinnamic acid halide (IV) and then deacetylated:

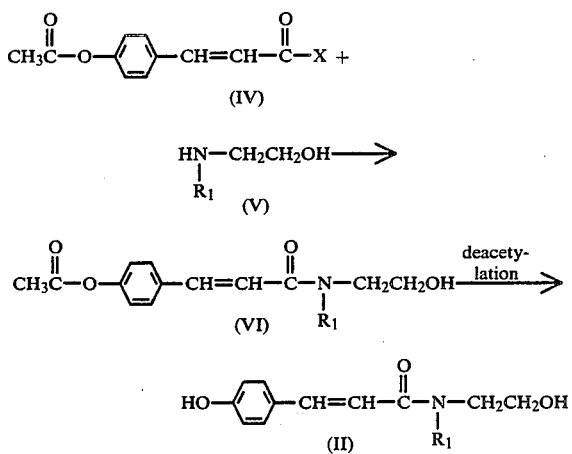

in which X represents a halogen atom, and $R_1$ has the same meaning as defined before.

The reaction between the compounds (IV) and (V) is effected according to a known amide preparation reaction. The reaction should preferably be carried out in the presence of a tertiary amine serving as an acid trapping agent or using the compound (V) in an amount higher than two mole equivalents to (IV) in order to serve also as an acid trapping agent. Examples of the tertiary amines used in the reaction include pyridine, triethylamine, tributylamine, picoline, quinoline and the like. The solvent used for the reaction is, for example, methylene chloride, chloroform or the like, but other solvents inert for the reaction may also be used. The reaction temperature is generally in the range of from $-20°$ C. to $100°$ C. Since the reaction proceeds exothermically, it is preferred to effect the reaction while cooling the system within a range of from $-10°$ C. to $30°$ C.

The resultant compound (VI) may be isolated and is preferably subjected to the subsequent deacetylation reaction without isolation. The deacetylation is carried out in an inert solvent such as methanol, ethanol or the like by reaction with a primary or secondary amine at a temperature of from $0°$ to $100°$ C, preferably from $30°$ to $60°$ C. Examples of the primary or secondary amine include methylamine, ethylamine, dimethylamine, diethylamine and the like.

The melanin inhibitors of the invention should generally contain the p-hydroxycinnamamide derivative (I) in an amount of from 0.01 to 50 wt. % (hereinafter referred to as %), preferably from 1 to 20%, and most preferably from 5 to 10%. The melanin inhibitor of the invention may take various forms such as a lotion, an emulsion, a cream, an ointment, a stick, a solution in organic solvents, a pack, a gel and the like.

The melanin inhibitor of the invention may further comprise other arbitrary ingredients ordinarily used in various cosmetics. Examples of the ingredients include oil substances, humectants, thickeners, preservatives, emulsifiers, medical ingredients, perfumes, emulsion stabilizers and the like. Moreover, the addition of other various ingredients such as allantoin, vitamin E acetate, glycyrrhizin, salicylic acid, urea, coix seed, and various plant extracts can enhance the melanin-inhibiting effect. Since the p-hydroxycinnamamide derivative (I) of the invention has the UV absorbing effect, other UV-absorbent can be added to obtain a melanin inhibitor having both the sunburn preventing and curing effects.

The thus obtained melanin inhibitors of the invention are locally applied onto affected parts such as spots and freckles on the skin, and a pigmental deposition after sunburn. The amount is preferably in the range of from 1 to 20 mg/cm$^2$ of the skin for cream and ointment preparations, and in the range of from 1 to 10 mg/cm$^2$ for liquid preparations.

The detailed mechanism of the p-hydroxycinnamamide derivative (I) with respect to the melanin inhibiting effect is not known. The local application of the melanin inhibitor of the invention to spots and freckles on the skin and a pigmental deposition site after sunburn can cure the sites, thereby returning to a normal skin color. In this sense, the inhibitor is completely different from known sunlight screening agent which is used to prevent sunburn.

The present invention is further described by way of test examples and examples.

EXAMPLE 1

Preparation of p-hydroxy-N,N-bis(2-hydroxyethyl)cinnamamide 24.5 g (233 mmol) of diethanolamine and 29.5 g (291 mmol) of triethylamine were dissolved in 150 ml of methylene chloride and stirred while keeping at 15°–20° C. A solution of 43.6 g (194 mmol) of p-acetoxycinnamoyl acid chloride in 200 ml of methylene chloride was dropped into the solution. Since heat generated upon the dropping, the reaction system was cooled while controlling the dropping rate to keep the temperature of the solution at 15°–20° C. After completion of the reaction, the system was stirred at room temperature for 1 hour. It was heated under reflux and stirred for 1 hour to complete the reaction. The methylene chloride was distilled off under reduced pressure, followed by addition of 100 ml of ethanol to the resultant viscous oil to make a substantially homogeneous solution. 29.5 g (380 mmol) of a 40% methylamine aqueous solution was added to the homogeneous solution at one time and stirred for 30 minutes after heating to 40°–50° C. The reaction solution was subjected to distillation under reduced pressure to remove the ethanol, which was diluted with 350 ml of water, followed by further addition of a 12% hydrochloric acid aqueous solution to an extent of a pH of about 3. The resultant crystals were separated by filtration and recrystallized from an ethanol/ethyl acetate mixed solvent, thereby obtaining 37.4 g of p-hydroxy-N,N-bis(2-hydroxyethyl)cinnamamide as colorless or slightly yellow crystals.

Yield: 77%
M.P.: 148° to 150° C.
NMR (DMSO-$d_6$)
δ 3.30–3.70 (8H, m, —N(CH—$_2$CH$_2$OH)$_2$)
4.72 (1H, bs, —CH$_2$OH)
4.84 (1H, bs, —CH$_2$OH)
6.79 (2H, d, J=8Hz, aromatic proton)
6.94 (1H, d, J=15Hz, C=CH—)
7.40 (1H, d, J=15Hz, C=CH—)
7.50 (2H, d, J=8Hz, aromatic proton)
9.80 (1H, bs, Ar-OH)
IR $\nu_{max}$(KBr) cm$^{-1}$
3530, 3280, 1650, 1580, 1525, 1475, 1390, 1320, 1280, 1250, 1220, 1180, 1095, 1055, 1020

Elemental analysis:
Calculated for $C_{13}H_{17}N_1O_4$: C 62.1; H 6.8: N 5.6
Found: C 61.9; H 7.1; N 5.8

EXAMPLE 2

Preparation of p-hydroxy-N-(2-hydroxyethyl)cinnamamide 43.6 g (194 mmol) of p-acetoxycinnamoyl chloride was added to 200 ml of methylene chloride and heated at 40° C. to make a homogeneous solution. The solution was cooled down to 15°–20° C., into which 35.5 g (582 mmol) of monoethanolamine was dropped. Since the system generated heat during the dropping, it was cooled and the dropping rate was so controlled that the liquid temperature was maintained at 15°–20° C. After completion of the dropping, the system was stirred at room temperature for 1 hour, and was then heated under reflux and stirred for further 1 hour to complete the reaction. After distillation of the methylene chloride under reduced pressure, 50 ml of ethanol was added so as to obtain a substantially homogeneous solution. Thereafter, 30.1 g (388 mmol) of a 40% methylamine aqueous solution was added to the system at one time, followed by heating to 40°–50° C. and stirring for 1 hour. The reaction solution was poured into 800 ml of water, to which a 12% hydrochloric acid aqueous solution was added to a pH of about 3. The resultant crystals were filtered off and recrystallized from acetone to obtain 24.9 g of p-hydroxy-N-(2-hydroxyethyl)cinnamamide as colorless or slightly yellow crystals.

Yield: 62%
M.P.: 149° to 151° C.
NMR (DMSO-$d_6$)
δ 3.10–3.70 (4 H, m, —N—CH$_2$CH$_2$—O—)
4.77 (1H, bs, —CH$_2$OH)
6.50 (1H, d, J=15Hz, C=CH—)
6.82 (2H, d, J=8Hz, aromatic proton)
7.37 (1H, d, J=15Hz, C=CH—)
7.41 (2H, d, J=8Hz, aromatic proton)
8.00 (1H, bs, NH)
9.80 (1H, bs, Ar-OH)
IR $\nu_{max}$ (KBr) cm$^{-1}$
3250, 1650, 1610, 1575, 1510, 1460, 1375, 1340, 1275, 1220, 1165, 1095, 1070, 980

Elemental analysis:
Calculated for $C_{11}H_{13}N_1O_3$: C 63.8; H 6.3; N 6.8
Found: C 64.1; H 6.1; N 6.9

TEST EXAMPLE 1

Effects of the present invention on pigmental spots of guinea pig induced by UV

Laboratory animals that can produce pigmental spot formability were used and subjected to pigmental deposition, followed by determination of an effect of improving the pigmental deposition. The results are shown in Table 1.

(Test Method)

The skin on the back of yellowish brown guinea pigs (whose skin color is alike to the yellow race and which commence to produce pigmental spots about 4 days after irradiation of UV rays similar to humans and is mostly melanized at about 8th day) was used. The hair on the back of the guinea pigs was cut with a hair clipper and then shaved with an electric shaver. The thus shaved back was covered with an aluminium foil having 6 square openings with a size of 1.5 cm × 1.5 cm and was irradiated with UV-B (consisting of 6 SE lamps of 3.0 mW/cm$^2$ at 305 nm) for 5 minutes once a day over three consecutive days.

About 3 weeks after the final irradiation, the resultant pigmental deposition sites were applied with a 10% sample solution (solvent: ethanol 80%+water 20%) twice a day over 38 days. The degree of the melanization of the skin was visually observed according to the following standards and the effect was evaluated as an average of the observed score. Evaluation standards:

—: 0 : any pigmental deposition was not recognized.
+: 1 : a slight degree of pigmental deposition with vague boundary.
+: 2 : a clear, moderate pigmental deposition was observed.
++: 3 : a clear, intense pigmental deposition was observed.

The results are shown in Table 1 below.

TABLE 1

| Sample | Prior to Application | After 38 days |
|---|---|---|
| p-hydroxy-N,N-bis(2-hydroxyethyl)-cinnamamide | 2.7 | 1.1 |
| p-hydroxy-N-(2-hydroxyethyl)-cinnamamide | 2.6 | 1.3 |
| control (80% ethanol alone) | 2.6 | 2.4 |

TEST EXAMPLE 2

The general procedure of Test Example 1 was repeated except that a 10% sample solution (solvent: ethanol 80%+water 20%) was applied from the 14th day after the final irradiation onto the pigmental deposition sites produced by the irradiation twice a day for 30 days. The results are shown in Table 2 below.

TABLE 2

| Sample | Prior to Application | After 30 days |
|---|---|---|
| N-(p-hydroxycinnamoyl)glycine | 2.8 | 1.1 |
| Control (80% ethanol alone) | 2.7 | 1.9 |

TEST EXAMPLE 3

Effect of this invention on human pigmental spots induced by UV rays

The effect of mitigating the pigmentary deposition of the compound (II) on humans was checked. The test method was as follows. The flexor side at the forearm of fifteen healthy men was covered with an aluminium foil having square openings with a size of 1.5 cm×1.5 cm and was continuously exposed to UV-A or UV-B (4 Osuram lamps, 2.6 mW/cm$^2$) for 1 to 3 minutes once a day over three consecutive days. From the 14th day, at which the degree of pigmentation have become maximum by the UV irradiation, an 80% ethanol solution containing 10% of the sample or a cream containing 10% of the sample (with similar formulations of Examples 4 and 5) was applied twice a day in an amount of 20 mg/225 cm$^2$. Four weeks after commencement of the application, the applied sites were compared with ethanol (80%) applied control sites and base cream (free of the sample) applied sites. The judgement was made according to the standards indicated in Test Example 1. The results are shown in Tabel 3.

TABLE 3

| Tested Person No. | Prior to Application | After Application of 40 Days | | |
|---|---|---|---|---|
| | | 10% p-hydroxy-N,N-bis(2-hydroxyethyl)-cinnamamide | 10% p-hydroxy-N-(2-hydroxyethyl)-cinnamamide | Control |
| 1 | ++ | ± | ± | + |
| 2 | ++ | ± | ± | + |
| 3 | ++ | − | ± | ± |
| 4 | + | − | − | ± |
| 5 | ++ | ± | + | ++ |
| 6 | ++ | ± | ± | + |
| 7 | ++ | − | − | ± |
| 8 | ++ | − | ± | ± |
| 9 | ++ | ± | ± | + |
| 10 | ++ | − | ± | ++ |
| 11 | + | − | − | + |
| 12 | ++ | ± | ± | + |
| 13 | ++ | ± | + | + |
| 14 | ++ | − | − | ± |
| 15 | ++ | − | ± | + |
| average | 2.87 | 0.47 | 0.87 | 1.80 |

TEST EXAMPLE 4

The effect of mitigating the pigmental deposition of the compound (III) on humans was checked.

The general procedure of Test Example 3 was repeated except that twenty healthy men were irradiated with UV-B (4 SE lamps, 2.1 mW/cm$^2$), a 80% ethanol solution containing 10% of compound (III), and the judgement was made 40th day after commencement of the application. The results are shown in Table 4.

TABLE 4

| | Prior to Application | After Application of 40 Days | |
|---|---|---|---|
| | | 10% N-(p-hydroxy-cinnamoyl)glycine | Control (80% ethanol) |
| Average | 2.8 | 1.1 | 2.3 |

EXAMPLE 3

| Lotion-type melanin inhibitor: | |
|---|---|
| p-hydroxy-N,N-bis(2-hydroxyethyl)-cinnamamide | 5 |
| Glycerin | 4 |
| Polyoxyethylene hardened castor oil | 1.5 |
| Ethanol | 10 |
| Sodium pyrrolidonecarboxylate | 2 |
| Perfume | very small amount |
| Purified water | balance |
| | 100% |

EXAMPLE 4

| Oil essence-type melanin inhibitor: | |
|---|---|
| p-hydroxy-N-(2-hydroxyethyl)-cinnamamide | 5 |
| Mink oil | 55 |
| Wheat germ oil | 40 |
| | 100% |

EXAMPLE 5

| Powder essence-type melanin inhibitor: | |
|---|---|
| p-hydroxy-N-(2-hydroxyethyl)-cinnamamide | 5 |
| Mannitol | 95 |
| | 100% |

EXAMPLE 6

W/O-type moisture cream-type melanin inhibitor:

| W/O-type moisture cream-type melanin inhibitor: | |
|---|---|
| p-hydroxy-N,N-bis(2-hydroxyethyl)-cinnamamide | 5 |
| Vaseline | 6 |
| Cholesterol | 0.6 |
| Cetyl alcohol | 0.5 |
| Sorbitan sesquioleate | 2 |
| Liquid lanolin | 4 |
| Isopropyl palmitate | 8 |
| Squalane | 10 |
| Solid paraffin | 4 |
| Butyl paraben | 0.1 |
| Methyl paraben | 0.1 |
| Glycerin | 3 |
| Perfume | 0.2 |
| Purified water | balance |
| | 100% |

EXAMPLE 7

O/W-type moisture cream-type melanin inhibitor:

| O/W-type moisture cream-type melanin inhibitor: | |
|---|---|
| p-hydroxy-N,N-bis(2-hydroxyethyl)-cinnamamide | 5 |
| Stearic acid | 2 |
| Cetyl alcohol | 4 |
| Vaseline | 5 |
| Squalane | 8 |
| Hardened palm oil | 4 |
| Polyoxyethylene(20)sorbitan monostearate | 1.4 |
| Oleophilic glycerine monostearate | 2.4 |
| Butyl paraben | 0.1 |
| Methyl paraben | 0.1 |
| Glycerin | 3 |
| Dipropylene glycol | 3 |

| O/W-type moisture cream-type melanin inhibitor: | |
|---|---|
| Potassium hydroxide | 0.2 |
| Perfume | 0.2 |
| Purified water | balance |
| | 100% |

EXAMPLE 8

| Emulsion-type melanin inhibitor: | |
|---|---|
| p-hydroxy-N-(2-hydroxyethyl)-cinnamamide | 5 |
| Stearic acid | 1 |
| Cetyl alcohol | 2 |
| Vaseline | 2.5 |
| Squalane | 4 |
| Hardened palm oil | 2 |
| Polyoxyethylene(20)sorbitan monostearate | 1.4 |
| Oleophilic glycerin monostearate | 1.2 |
| Butyl paraben | 0.1 |
| Methyl paraben | 0.1 |
| Glycerin | 3 |
| Dipropylene glycol | 3 |
| Potassium hydroxide | 0.2 |
| Carboxy vinyl polymer | 0.2 |
| Perfume | 0.2 |
| Purified water | balance |
| | 100% |

EXAMPLE 9

| Lotion-type melanin inhibitor: | |
|---|---|
| N-(p-hydroxycinnamoyl)glycine | 5 |
| Glycerin | 4 |
| Polyoxyethylene hardened castor oil | 1.5 |
| Ethanol | 10 |
| Sodium pyrrolidonecarboxylate | 2.0 |
| Perfume | very small amount |
| Purified water | balance |
| | 100% |

EXAMPLE 10

| Oil essence-type melanin inhibitor: | |
|---|---|
| N-(p-hydroxycinnamoyl)glycine | 5 |
| Mink oil | 55 |
| Wheat germ oil | 40 |
| | 100% |

EXAMPLE 11

| Powder essence-type melanin inhibitor: | |
|---|---|
| N-(p-hydroxycinnamoyl)glycine | 5 |
| Mannitol | 95 |
| | 100% |

EXAMPLE 12

| W/O-type moisture cream-type melanin inhibitor: | |
|---|---|
| N-(p-hydroxycinnamoyl)glycine | 5 |
| Vaseline | 6 |
| Cholesterol | 0.6 |
| Cetyl alcohol | 0.5 |

| W/O-type moisture cream-type melanin inhibitor: | |
|---|---|
| Sorbitan sesquioleate | 2.0 |
| Liquid lanolin | 4.0 |
| Isopropyl palmitate | 8.0 |
| Squalane | 10.0 |
| Solid paraffin | 4.0 |
| Butyl paraben | 0.1 |
| Methyl paraben | 0.1 |
| Glycerin | 3.0 |
| Perfume | 0.2 |
| Purified water | balance |
| | 100% |

EXAMPLE 13

| O/W type moisture cream-type melanin inhibitor: | |
|---|---|
| N-(p-hydroxycinnamoyl)glycine | 5 |
| Stearic acid | 2 |
| Cetyl alcohol | 4 |
| Vaseline | 5 |
| Squalane | 8 |
| Hardened palm oil | 4 |
| Polyoxyethylene(20)sorbitan monostearate | 1.4 |
| Oleophilic glycerin monostearate | 2.4 |
| Butyl paraben | 0.1 |
| Methyl paraben | 0.1 |
| Glycerin | 3.0 |
| Dipropylene glycol | 3.0 |
| Potassium oxide | 0.2 |
| Perfume | 0.2 |
| Purified water | balance |
| | 100% |

EXAMPLE 14

| Emulsion-type melanin inhibitor: | |
|---|---|
| N-(p-hydroxycinnamoyl)glycine | 5 |
| Stearic acid | 1 |
| Cetyl alcohol | 2 |
| Vaseline | 2.5 |
| Squalane | 4.0 |
| Hardened palm oil | 2.0 |
| Polyoxyethylene(20)sorbitan monostearate | 1.4 |
| Oleophilic glycerin monsterate | 1.2 |
| Butyl paraben | 0.1 |
| Methyl paraben | 0.1 |
| Glycerin | 3.0 |
| Dipropylene glycol | 3.0 |
| Potassium hydroxide | 0.2 |
| Carboxy vinyl polymer | 0.2 |
| Perfume | 0.2 |
| Purified water | balance |
| | 100% |

EXAMPLE 15

| Pack-type (pasty peel-off type) melanin inhibitor: | |
|---|---|
| N-(p-hydroxycinnamoyl)glycine | 10 |
| Polyvinyl alcohol | 12 |
| Sodium carboxymethyl cellulose | 3 |
| Dipropylene glycol | 2 |
| Glycerin | 2 |
| Ethanol | 5 |
| Olive oil | 3 |
| Polyoxyethylene hardened castor oil (30 E.O. units) | 0.5 |
| Titanium oxide | 8 |
| Kaolin | 6 |

-continued

| Pack-type (pasty peel-off type) melanin inhibitor: | |
|---|---|
| Perfume | 0.1 |
| Methyl paraben | 0.1 |
| Purified water | balance |
| | 100% |

EXAMPLE 16

| Ointment-type melanin inhibitor: | |
|---|---|
| N-(p-hydroxycinnamoyl)glycine | 10 |
| White vaseline | 90 |
| | 100% |

EXAMPLE 17

| Liquid-type melanin inhibitor: | |
|---|---|
| N-(p-hydroxycinnamoyl)glycine | 10 |
| Ethanol | 90 |
| | 100% |

What is claimed is:

1. A melanin inhibitor composition, comprising an active component of p-hydroxycinnamamide derivative of the formula:

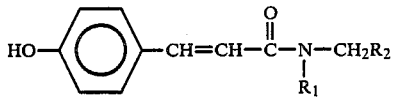

wherein $R_1$ is hydrogen or a 2-hydroxyethyl group, and $R_2$ is a carboxyl group in a cosmetically acceptable vehicle.

* * * * *